United States Patent [19]

Harmsen

[11] Patent Number: 4,599,812
[45] Date of Patent: Jul. 15, 1986

[54] LEGGINGS

[76] Inventor: Wayne A. Harmsen, 607 Morris St., Fond du Lac, Wis. 54935

[21] Appl. No.: 787,057

[22] Filed: Oct. 15, 1985

[51] Int. Cl.$^4$ ................................................ A43B 3/00
[52] U.S. Cl. ...................................... 36/1.5; 36/2 R; 2/239
[58] Field of Search ............... 2/239, 242, 61, DIG. 6; 36/2 R, 1.5, 110, 7.2, 83

[56] References Cited

U.S. PATENT DOCUMENTS

| | | | |
|---|---|---|---|
| 2,230,380 | 2/1941 | Johst | 36/2 |
| 2,493,878 | 1/1950 | Kirtz | 2/61 |
| 3,497,875 | 3/1970 | Rivera | 2/239 |
| 3,605,122 | 9/1971 | Myers | 2/239 |
| 4,008,531 | 2/1977 | Schonbrun et al. | 36/2 |

*Primary Examiner*—Ronald Feldbaum
*Attorney, Agent, or Firm*—Donald Cayen

[57] ABSTRACT

A warm and inexpensive legging is manufactured from a single piece of material. The material is cut into a blank having a generally rectangular leg section and a generally trapezoidal foot section. The leg and foot sections are separated by V-shaped darts in the periphery of the blank, the points of which are joined by a transverse fold line of material. The blank is folded along the fold line until the respective margins of the darts abut, and the margins are sewn to each other. The foot section is folded along a longitudinal fold line, and the edges are sewn together, thereby forming a foot enclosure. The leg section extends up the leg of a wearer. The longitudinal edges of the leg section wrap around the wearer's leg and are loosely joined by adjustable releasable fasteners.

18 Claims, 6 Drawing Figures

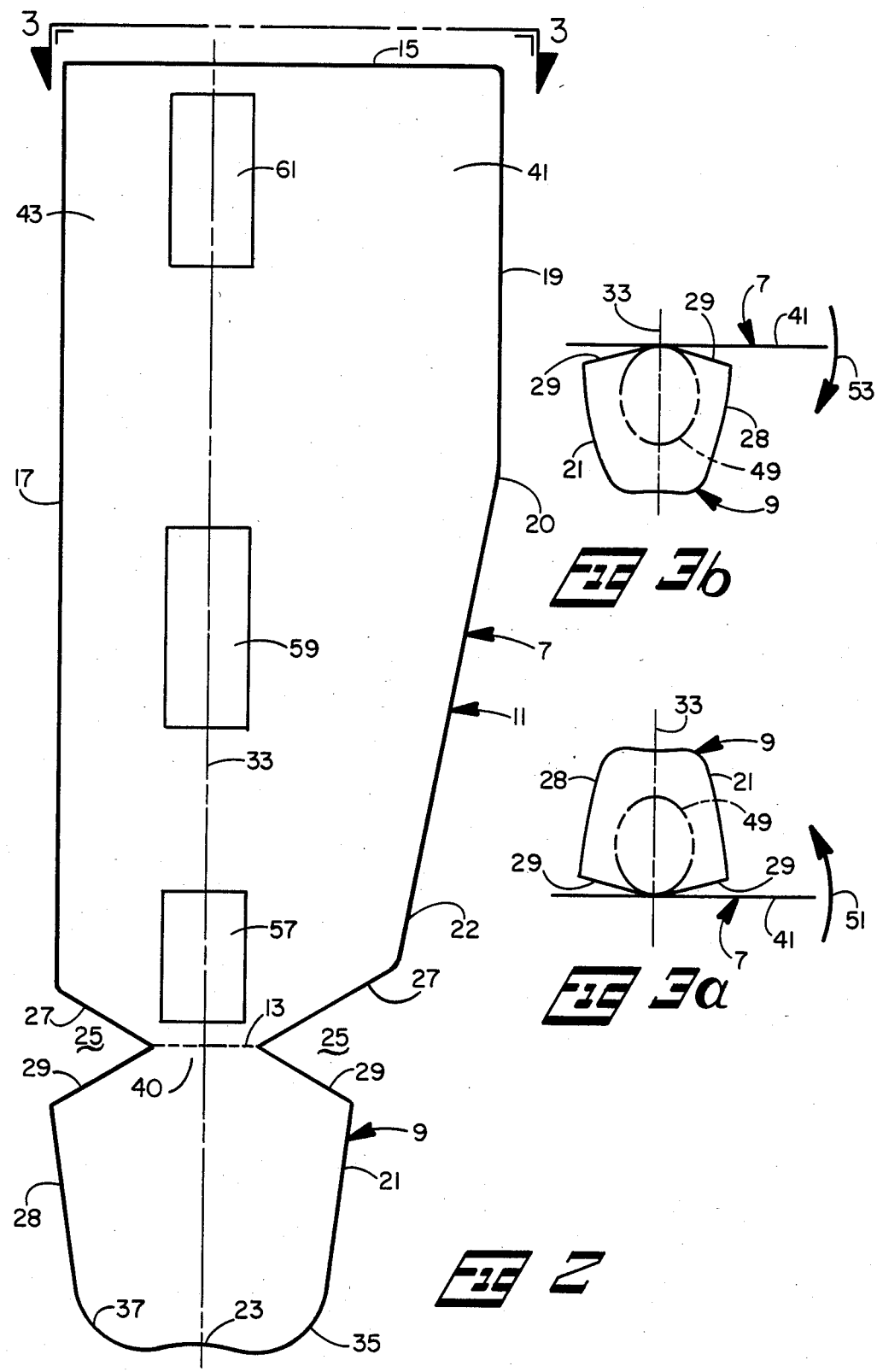

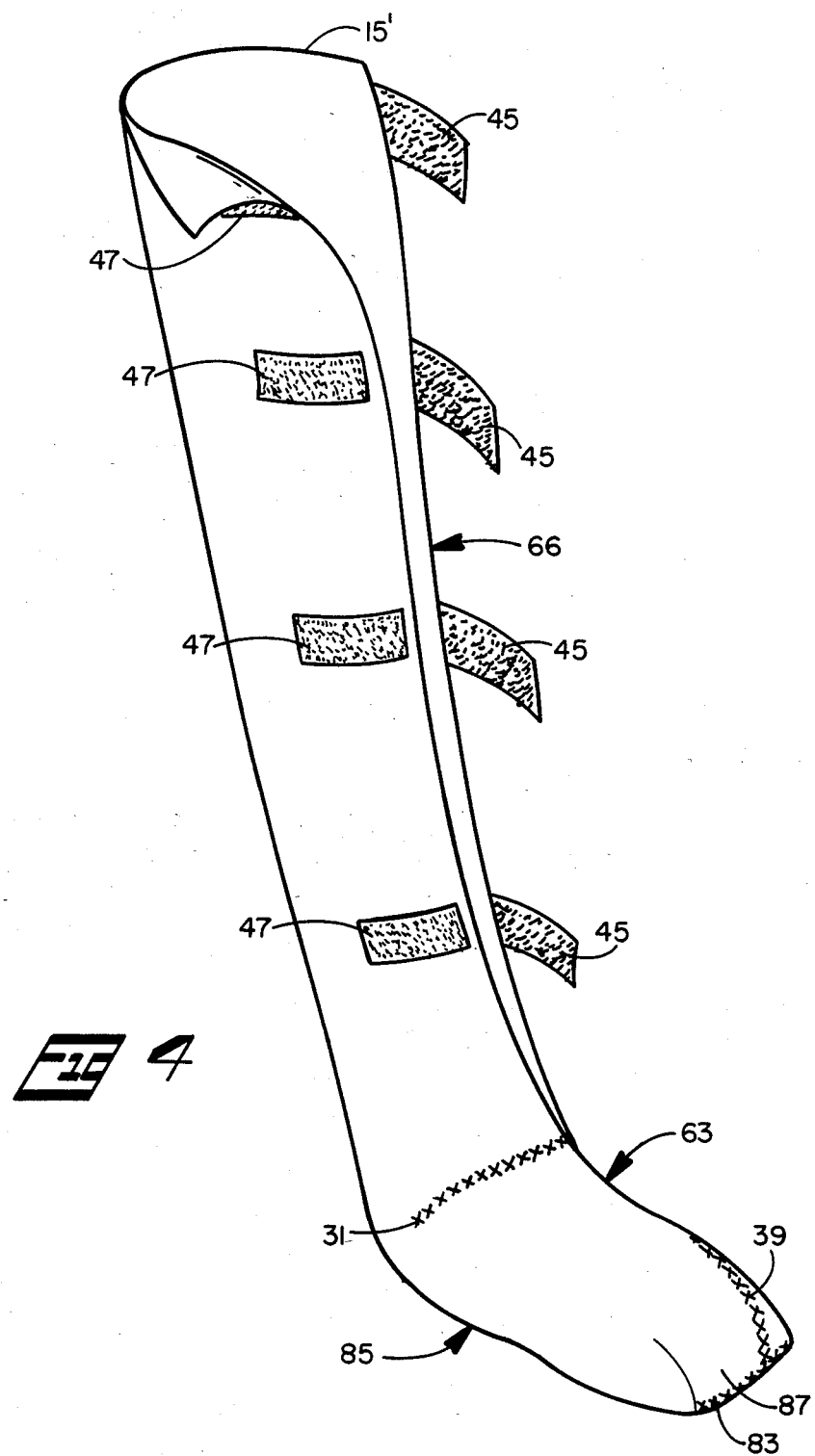

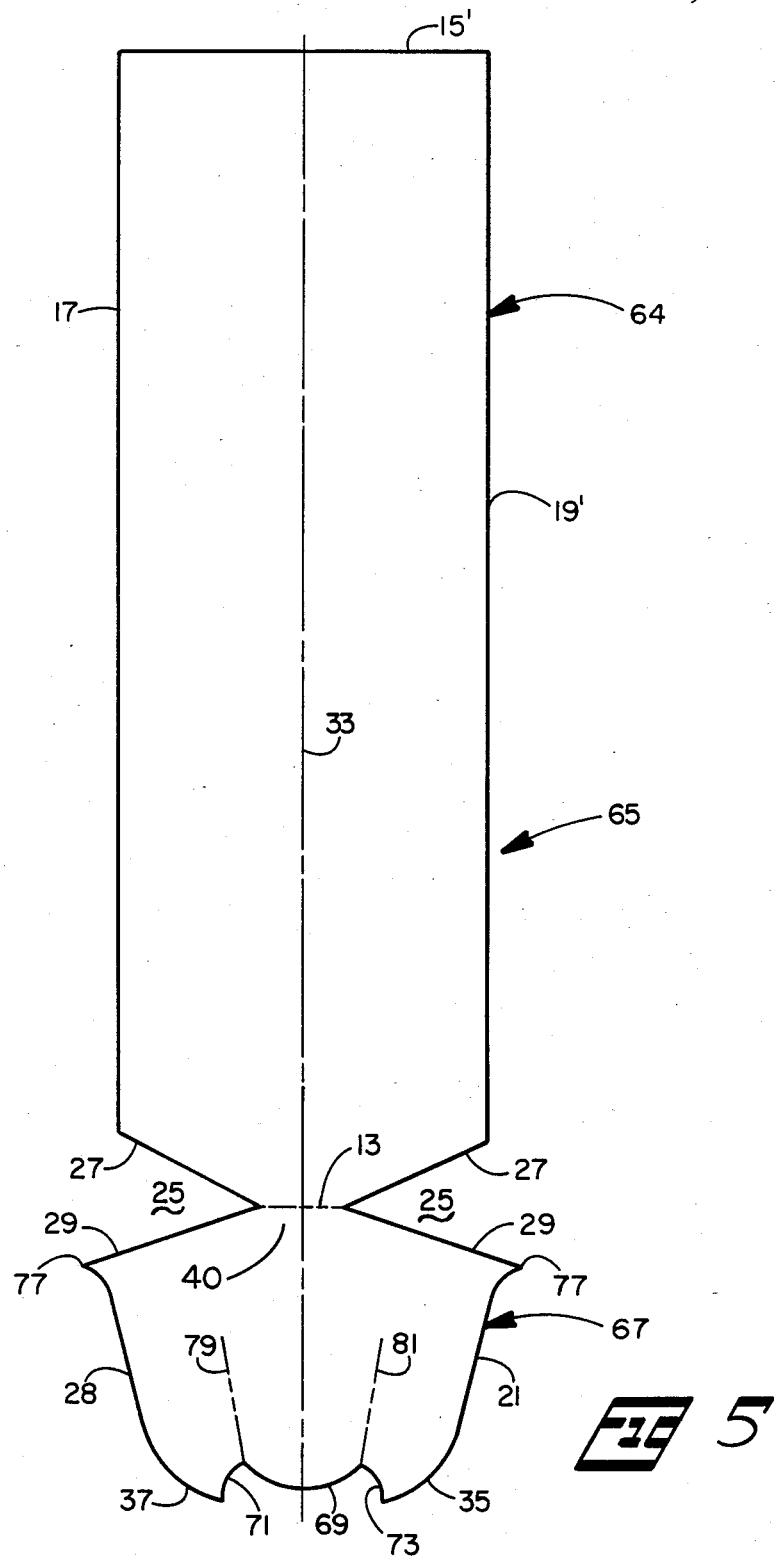

LEGGINGS

BACKGROUND OF THE INVENTION

1. Field of the Invention

The present invention pertains to garments, and more particularly to warm and comfortable garments for covering the feet and legs.

2. Description of the Prior Art

Numerous types of articles have been developed to cover and enhance the comfort of the human foot and leg. For example, medically related stockings such as those disclosed in U.S. Pat. Nos. 3,605,122 and 3,828,369 are in common use. Various designs of shoes and socks are well known, as are cast covers such as shown in U.S. Pat. No. 3,416,518. U.S. Pat. No. 1,457,590 shows two pieces of material sewn together to form a stocking having a seamless heel. It is evident that none of the mentioned kinds of clothing articles combine warmth, comfort, and low cost.

Warm and comfortable footwear is very important to those many people whose feet have a tendency to feel cold even when the rest of the body is comfortable. Knit or crocheted booties are commercially available, but they are expensive and cover only the foot and ankle. Relatively warm long stockings are also available, but invariably they include elastic material to hold the stocking in place. The elastic restricts the blood circulation within the feet and legs, thus making the feet feel cold and cancelling the benefit desired from wearing the stocking. Further, known stockings are not readily adjustable so as to fit comfortably without binding on people having different sized legs.

Thus, a need exists for a warm and economical stocking that is comfortable to different size wearers.

SUMMARY OF THE INVENTION

In accordance with the present invention, inexpensive and cozy leggings are provided that are adjustable to permit normal blood circulation even in elderly and sedentary persons. This is accomplished by manufacturing the leggings from a single piece of flexible insulative material that is cut and sewn in a novel manner.

The legging material may be a cotton or wool flannel or similar warm and comfortable material. The material is cut into a blank according to a simple pattern. The blank is designed in a generally rectangular shape that is folded and sewn so as to enclose the foot and a selected portion of the leg. The blank comprises a leg section and a foot section. The leg section has a length about equal to the distance from the heel to the desired point on the leg calf or thigh. The top edge of the leg section has a length that is greater than the circumference of the calf or thigh. A first longitudinal edge extends at substantially a right angle to the top edge. A second longitudinal edge extends at a right angle from the top edge and then angles in a direction that converges toward the first longitudinal edge in the direction of the lower end of the leg section.

The lower end of the blank leg section connects with the upper end of the foot section. The foot section is preferably cut with a pair of downwardly converging side edges that blend through large radii into a slightly concave bottom edge, thereby forming a generally trapezoidal shape. The distance from the common line between the leg and foot sections to the bottom edge of the foot section corresponds to the length of a foot from the heel to the toes. The width of the foot section between the converging side edges is sized to enclose the foot when wrapped around the foot. The foot and leg sections are partially separated by a pair of V-shaped darts cut in the blank periphery and extending inwardly therefrom.

To make a legging from the blank, the margins of each dart are sewn together, thus causing the material at the junction of the leg and foot sections to fold transversely so that the foot section extends at an angle from the leg section. The width of the darts is chosen such that the angle between the foot and leg sections is slightly greater than 90 degrees. The foot section is then folded in half longitudinally, and the edge on one side of the fold line is sewn to the edge on the other side of the fold line. With that step, a foot enclosure is created, but an opening remains for inserting the foot into the enclosure. With the creation of the foot enclosure from the blank foot section, the blank leg section is transformed into a leg wraparound for enclosing the wearer's leg.

To comfortably retain the legging of the present invention on the wearer's leg, suitable adjustable fasteners are attached to the leg wraparound. The fasteners may be several dual strip Velcro fasteners, with one strip sewn near each longitudinal edge of the leg section. Because the upper edge of the blank leg section is wider than the circumference of the wearer's leg, the longitudinal edges of the leg wraparound overlap when the legging is wrapped around the leg, thus forming a covering flap. The Velcro strips permit adjusting the overlap to suit the wearer. Thus, the legging of the present invention may be custom fit to the wearer's leg, thereby keeping his foot and leg warm without excessive tightness or looseness.

The same blank may be used for both right and left hand leggings. Opposite hands are created merely by transversely folding the foot section in opposite directions with respect to the leg section prior to sewing the dart margins together.

To provide greater stability to the flap, a facing material may be sewn to the inside thereof. The legging may be decorated as desired. The leg and foot sections may be of different sizes to suit different size wearers. Extra large sizes may be made for use as cast covers.

In a modified embodiment of the present invention, the top edge of the leg wraparound is approximately equal to the circumference of the wearer's leg, and the longitudinal edges of the leg wraparound lie approximately equidistant from the longitudinal fold line, thus eliminating the leg wraparound flap. With that embodiment, the overlapping of one longitudinal edge by the other is reduced or eliminated.

In a further modification of the present invention, the bottom edge of the foot section is cut with a centrally located notch. The notch may have a convex base interposed between a pair of concave sides. Each concave side is sewn to a corresponding portion of the convex base, and then the foot section is folded in half longitudinally so that the converging side edges thereof may be sewn together. The result is an attractive foot enclosure having a horizontally oriented toe section that comfortably receives the wearer's toes.

Other advantages and features of the invention will become apparent to those skilled in the art from the disclosure.

BRIEF DESCRIPTION OF THE DRAWINGS

FIG. 2 is a front view of a blank of material from which the legging of the present invention may be manufactured;

FIGS. 3a and 3b are reduced views taken along lines 3—3 of FIG. 2, but showing the blank partially folded in opposite directions for making leggings of opposite hands.

FIG. 4 is a perspective view of a modified embodiment of the present invention; and FIG. 5 is a front view of a blank of material from which the legging of FIG. 4 may be manufactured.

DETAILED DESCRIPTIN OF THE INVENTION

Figure 1:
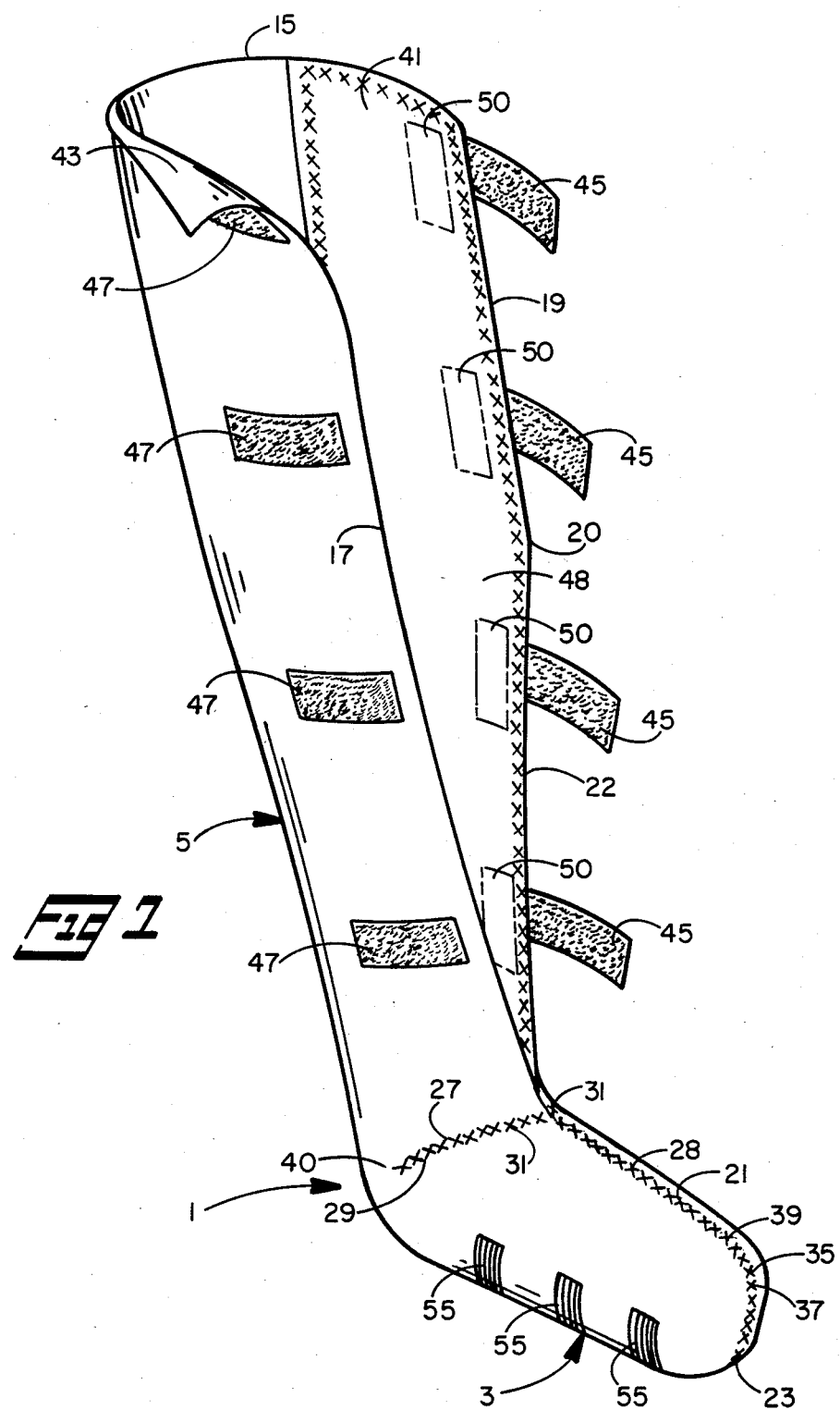
FIG. 1 is a perspective view of the legging of the present invention.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Referring to FIG. 1, a legging 1 is illustrated that includes the present invention. The legging is particularly useful for keeping warm the foot and leg of a person, but it will be understood that the invention is not limited to leg and foot applications.

The legging 1 comprises a foot enclosure 3 and a leg wraparound 5. FIG. 2 illustrates a blank 7 of material from which the legging 1 is preferably manufactured. The blank 7 includes a foot section 9 and a leg section 11 that correspond with the foot enclosure 3 and leg wraparound 5, respectively (FIG. 1). The foot section 9 and leg section 11 are joined along a transverse fold line 13, FIG. 2.

The leg section 11 has an upper edge 15 that is longer than the circumference of a person's thigh or calf. The distance from the top edge 15 to the fold line 13 determines the length of the legging wraparound 5. Three lengths are considered to be sufficient—below the knee, above the knee, and full length to the crotch. A first longitudinal edge 17 extends at approximately a right angle from the upper edge 15. A second longitudinal edge 19 has an upper portion that extends from the upper edge at approximately a right angle, and then bends at 20 into a lower portion 22 that converges toward the first longitudinal edge 17 in the direction of the foot section 9. The lower end of the leg section is defined by fold line 13 and by lower margins 27. Each lower margin 27 defines one side of a V-shaped dart 25 cut into the blank 7 and extending inwardly from the longitudinal edges 17 and 22.

In the illustrated construction, the foot section 9 of the blank 7 is cut with a pair of downwardly converging side edges 21, 28 that blend through large radii 35, 37, respectively, into a slightly concave bottom edge 23. The distance from the fold line 13 to the bottom edge 23 corresponds to the length of the foot from the heel to the toes. The upper end of the foot section is defined by the fold line 13 and by margins 29 of the darts 25. Thus, the blank material is continuous in the region 40 between the foot and leg sections at the fold line 13.

To manufacture the legging 1 from the blank 7 according to the present invention, the blank is folded along fold line 13 such that the associated margins 27 and 29 of the darts 25 are brought into contact. The associated margins are joined together, as, for example, by sewing along stitchings 31. See FIG. 1. The amount of the folding between the foot and leg sections is determined by the width of the darts. It is generally preferred that the darts be sized such that the angle between the foot and leg sections be somewhat greater than 90 degrees. Thus, a preferred included angle for the darts is about 75 degrees. The foot section 9 of the blank is then folded along longitudinal fold line 33. The converging edges 21 and 28 and the radius portions 35 and 37, as well as the portions of the bottom edge 23 on either side of the fold line 33, are brought together and fastened, as by sewing along stitchings 39, FIG. 1. As a result, the foot enclosure 3 is formed, together with the leg wraparound 5. The darts are preferably located such that the stitchings 31 joining the respective margins of the darts lie diagonally below the ankle.

It will be recognized that an opening into the foot enclosure 3 from the leg wraparound 5 is created by the combination of the stitchings 31 and 39 for receiving the wearer's foot, not shown in FIG. 1. Further, the blank material in the region 40 of the fold line 13 forms the heel of the legging 1, the leg wraparound extends up the wearer's leg.

As shown in FIG. 2, the top edge 15 of the blank 7 lies unsymetrically about the longitudinal fold line 33. Thus, a flap 41 is formed that is defined generally by edges 15 and 19. Since length of the top edge is longer than the circumference of the wearer's thigh or calf, the flap 41 overlaps the underlying region 43 defined generally by edges 15 and 17 when the wearer wraps the leg wraparound 5 around his leg.

To comfortably retain the legging 1 of the present invention on the wearer's leg, a series of adjustable releasable fasteners are employed. In the preferred embodiment, the fasteners consist of two or more pairs of Velcro strips 45, 47 spaced longitudinally along the edges 17, 19, and 22, FIG. 1. The first strips 45 of each pair may be horizontally oriented and are attached to the outside surface of the 41 and extend beyond the edges 19 and 22. The second strips 47 are joined to the outside surface of the underlying region 43 such that the first strips releasably adhere to the strips 47 when the leg wraparound 5 is wrapped around the wearer's leg. Alternately, the first Velcro strips may be joined to the inside surface of the flap 41, as shown at reference numerals 50. To provide additional ease of fastening the legging, the strips 50 may be oriented vertically rather than horizontally. Thus, legging 1 may be worn as loosely as desired without coming open. Accordingly, the legging keeps the wearer's foot and leg warm without restricting blood circulation.

It is a feature of the present invention that a single design of the blank 7 can be used to fabricate leggings 1 of opposite hand. Opposite hand leggings are produced merely by folding the foot section 9 in opposite directions with respect to leg section 7 along fold line 13. For example, referring to FIGS. 2 and 3a, the foot section may be folded into the plane of the drawing and sewn as previously described. Under that situation, the flap 41 will wrap around the wearer's leg 49 in the direction of arrow 51. Thus, the flap 41 wraps in a counterclockwise direction around the leg 49 to form a left hand legging. Alternately, the foot section may be folded out from the plane the drawing of FIG. 2. In that case, the configuration of FIG. 3b results, and the flap 41 wraps clockwise, arrow 53, around the wearer's leg to form a right hand legging.

The preferred material for the legging 1 is a warm and comfortable cotton or wool flannel. To provide increased tody for thin materials, the inside of the flap 41 may have a facing 48 sewn thereto, as illustrated in FIG. 1. For greater warmth, the entire legging, or any desired portion thereof, may be lined with fleece. Both the foot enclosure 3 and leg wraparound 5 may be of varying sizes to suit different size wearers. To provide comfort to bedridden persons susceptible to bed sores, pieces of sheepskin may be sewn to appropriate areas on the legging. As shown in FIG. 2, pieces of sheepskin 57, 59, and 61 may be sewn to the legging areas that correspond with the backs of the heel, calf, and thigh, respectively. Both the foot enclosure and leg wraparound may be disproportionately large, so that the leggings may be used as cast covers or for covering the feet and legs of spectators at cold weather sporting events. The legging is admirably suited as a liner for firemen's boots and sportsmen's hip boots and as a warm covering for an athlete with a foot or leg injury. The legging may be made into a very attractive garment by the use of decorations. For example, a strip of beading may be sewn to edges 15, 19, and 22. To aid in walking with the legging in place, conventional strips of friction material 55 may be secured to the underside of the foot enclosure, as by sewing, or by employing a suitable adhesive or heat sealing method. Alternately, a flexible sole of rubber like material may be bonded to the entire underside of the foot enclosure.

Referring to FIG. 4, a modified embodiment of the present invention is disclosed. The modified legging 63 is made from a blank 65, FIG. 5. The leg section 64 of the blank 65 corresponds with leg wraparound 66 and has a top edge 15' that has a length approximately equal to the circumference of the wearer's leg. The first and second longitudinal edges 17 and 19' are substantially parallel and are approximately equidistant from the longitudinal fold line 33.

The foot section 67 of the blank 65 is defined by downwardly converging side edges 21 and 28 that blend via large radii 35 and 37 into bottom edge 69. The junctions of the side edges and margins may be cut as protruding points 77. Bottom edge 69 is formed with a notch having a pair of side edges 71 and 73 with an intermediate base 75. In the illustrated construction, the side edges 71 and 73 have slightly concave contours and intermediate base 75 has a slightly convex contour.

To create the legging 63 from the blank 65, the corresponding margins 27 and 29 of the darts 25 are sewn together along stitch lines 31 as previously described. The leg section 64 is then folded generally along fold lines 79 and 81 such that the concave edges 71 and 73 are contiguous with the convex base 75 on either side of the fold line 33. The contiguous edges are sewn together to create a horizontal stitch line 83, FIG. 4. The leg section is then folded along fold line 33 to bring the pairs of edges 21, 28 and 35, 37 together; the pairs of edges are then sewn together along stitchings 39, FIG. 4. The resulting foot enclosure 85 thus has a horizontally oriented toe portion 87 bounded in part by the stitchings 83. Velcro strips 45 and 47 are utilized in the same manner as with legging 1, as previously described.

It will be understood that the features and uses of the legging 63 are substantially identical to those of legging 1. It will also be understood that the various constructions of the foot enclosures 3 and 85 are interchangeable with the leg wraparounds 5 and 66. That is, foot enclosure 85 may be used with leg wraparound 5, and foot enclosure 3 may be used with leg wraparound 66.

Thus, it is apparent that there has been provided, in accordance with the invention, a legging that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A legging for wearing on a human leg and foot and made from a single piece of material comprising:
   a. a leg wraparound adapted to cover at least a portion of a leg and defined by a top edge, a lower end having a region of material interposed between first and seccond laterally spaced lower margins, and first and second longitudinal edges extending between the top edge and the respective lower margins;
   b. a foot enclosure adapted to cover a foot and defined by a pair of converging side edges and a bottom edge and an upper end having a region of material interposed between first and second upper margins that correspond with the respective lower margins of the leg wraparound, the region of material of the foot enclosure being continuous with the region of material of the leg wraparound, the converging side dges and bottom edge being fastened to enclose the foot, the upper margins being joined to the respective lower margins of the leg wraparound to join the foot enclosure to the leg wraparound; and
   c. fastening means for releasably fastening the leg wraparound longitudinal edges to each other when the legging is in place on a wearer's foot and leg.

2. The legging of claim 1 wherein the longitudinal edges overlap when the leg wraparound is wrapped around the leg of the wearer.

3. The legging of claim 1 wherein:
   a. the leg wraparound top edge is longer than the circumference of the wearer's leg;
   b. the first longitudinal edge extends at substantially a right angle from the top edge; and
   c. the second longitudinal edge defines an upper portion that extends at about a right angle from the top edge and a lower portion that converges toward the first longitudinal edge in the direction of the foot enclosure, so that a flap is created in the region defined by the leg wraparound top edge and the second longitudinal edge upper portion for overlapping the first longitudinal edge when the legging is wrapped around the leg of the wearer.

4. The legging of claim 1 wherein the foot enclosure further comprises at least one strip of friction material secured to the underside of the foot enclosure to thereby aid in walking with the legging in place.

5. The legging of claim 1 wherein the leg wraparound includes a facing attached to at least a portion of the interior surface of the legging to thereby provide increased body to the legging.

6. The legging of claim 1 wherein the legging wraparound top edge is approximately equal to the circumference of the wearer's leg, and wherein the first and second longitudinal edges extend at substantially right angles from the top edge.

7. The legging of claim 1 further comprising a piece of sheepskin fastened to the legging in at least one area corresponding with the back of the heel, calf, and thigh of the wearer.

8. A blank of material useful for forming into a legging for covering a human foot and leg comprising:
 a. a generally rectangular shaped leg section having a transverse top edge, a lower end defined by a transverse fold line interposed between a pair of lower margins, and first and second side edges extending generally longitudinally between the top edge and the lower margins; and
 b. a foot section having side and bottom edges and an upper end defined by a transverse fold line coincident with the fold line of the leg section and a pair of upper margins corresponding with the respective lower margins of the leg section, the respective lower margins of the leg section and upper margins of the foot section forming a pair of V-shaped darts cut into the periphery of the blank.

9. The blank of claim 8 wherein the transverse top edge of the leg section is longer than the circumference of the leg of a wearer.

10. The blank of claim 8 wherein:
 a. the first longitudinal side edge extends at substantially a right angle to the top edge; and
 b. the second longitudinal side edge defines an upper portion that extends at about a right angle from the top edge and a lower portion that extends from the upper portion in a direction that converges with the first longitudinal side edge in the direction of the foot section.

11. The blank of claim 8 wherein the foot section side edges converge downwardly from the respective upper margins and arcuately blend into the bottom edge, and wherein the bottom edge is slightly concave.

12. The blank of claim 11 wherein the longitudinal length between the transverse fold line and the foot section bottom edge is approximately equal to the length of the foot of a wearer.

13. The blank of claim 8 wherein:
 a. the leg section top edge is approximately equal to the circumference of a wearer's leg; and
 b. the first and second longitudinal edges extend at substantially right angles from the top edge.

14. The blank of claim 8 wherein the foot section side edges converge downwardly from the respective upper margins and the bottom edge is formed with a notch having an intermediate base interposed between a pair of side edges, each side edge terminating at an arcuate contour that blends into the respective converging side edges.

15. The blank of claim 14 wherein the intermediate base of the foot section notch is convex and the side edges of the foot section notch are concave.

16. A method of manufacturing a legging to be worn on a human leg and foot comprising the steps of:
 a. providing a blank of material having a generally rectangular shaped leg section and a generally trapedzoidal shaped foot section, the material of the leg and foot sections being common along a transverse fold line, the blank defining a pair of V-shaped darts extending inwardly from the blank periphery and having the points thereof lying on the transverse fold line;
 b. folding the blank along the transverse fold line to bring the respective margins of the darts together;
 c. joining the respective margins of the darts to each other;
 d. folding the foot section longitudinally to bring the edges of the foot section into contiguous contact;
 e. joining the foot section edges to each other to create a foot enclosure; and
 f. attaching at least one adjustable releasable fastener to the leg section for enabling the leg section to be held in place when the leg section is wrapped around a wearer's leg.

17. The method of claim 16 wherein the step of folding the blank along the transverse fold line includes folding the foot section to an angle with respect to the plane of the leg section that is greater than a right angle.

18. The method of claim 16 wherein the step of folding the blank along the transverse fold line includes the step of folding the foot section in either direction with respect to the plane of the blank leg section.

* * * * *